(12) United States Patent
Maramaldi et al.

(10) Patent No.: US 11,744,793 B2
(45) Date of Patent: Sep. 5, 2023

(54) COSMETIC COMPOSITIONS FOR PROTECTION AGAINST AIR POLLUTANTS

(71) Applicant: Indena S.P.A., Milan (IT)

(72) Inventors: Giada Maramaldi, Milan (IT); Martino Meneghin, Milan (IT); Federico Franceschi, Milan (IT); Stefano Togni, Milan (IT); Salvatore Malandrino, Milan (IT)

(73) Assignee: GIVAUDAN ITALIA S.P.A., Vimodrone (IT)

( * ) Notice: Subject to any disclaimer, the term of this patent is extended or adjusted under 35 U.S.C. 154(b) by 790 days.

(21) Appl. No.: 16/090,653

(22) PCT Filed: Apr. 6, 2017

(86) PCT No.: PCT/EP2017/058247
§ 371 (c)(1),
(2) Date: Oct. 2, 2018

(87) PCT Pub. No.: WO2017/174718
PCT Pub. Date: Oct. 12, 2017

(65) Prior Publication Data
US 2020/0323767 A1    Oct. 15, 2020

(30) Foreign Application Priority Data

Apr. 8, 2016 (IT) .................. 102016000036493

(51) Int. Cl.
| | | |
|---|---|---|
| *A61K 8/9789* | (2017.01) | |
| *A61K 8/49* | (2006.01) | |
| *A61Q 5/00* | (2006.01) | |
| *A61Q 19/00* | (2006.01) | |

(52) U.S. Cl.
CPC ............ *A61K 8/9789* (2017.08); *A61K 8/498* (2013.01); *A61Q 5/00* (2013.01); *A61Q 19/001* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 5,686,082 A | 11/1997 | N'Guyen | |
| 2004/0013696 A1 | 1/2004 | Duche et al. | |
| 2004/0037857 A1 | 2/2004 | Catroux et al. | |
| 2006/0062861 A1* | 3/2006 | Wille | A61Q 19/00 424/729 |
| 2011/0086116 A1 | 4/2011 | Florence et al. | |
| 2011/0281941 A1* | 11/2011 | Manissier | A61P 17/00 514/458 |

FOREIGN PATENT DOCUMENTS

| | | |
|---|---|---|
| CN | 105030584 A | 11/2015 |
| CN | 105263583 A | 1/2016 |
| DE | 102007031452 A1 | 1/2009 |
| FR | 2981272 A1 | 4/2013 |
| FR | 3013220 A1 | 5/2015 |
| JP | 2003533459 A | 11/2003 |
| JP | 2003533461 A | 11/2003 |
| RU | 2491009 C2 | 8/2013 |
| WO | 2012065651 A1 | 5/2012 |

OTHER PUBLICATIONS

Clausen et al., Heavy metal air pollution among autoworkers, I. Lead, 1977, British J Industrial Medicine, 34: 208-215.*
Database GNPD MINTEL; "Eye Lift + Circle Reducer", Jul. 31, 2011.
International Preliminary Report on Patentability of PCT/EP2017/058247 dated Jun. 18, 2018.
Search Report and Written Opinion of PCT/EP2017/058247 dated Jun. 6, 2017.
Tchounwou P.B., et al., "Heavy metals toxicity and the environment", NIH Public Access Aug. 26, 2014.
Letter of Russian correspondent dated Jun. 23, 2020 reporting office action, search report and cited reference for Russian patent application No. 2018137684.
Office Action issued in corresponding Russian patent application.: 2018137684/04(062483 dated May 29, 2020.
Search Report cited in corresponding Russian patent application 2018137684 dated May 28, 2020.
Office Action dated Feb. 19, 2021 in connection with corresponding Japanese patent application No. 2018-552852.
Office Action dated Nov. 15, 2020 in connection with corresponding Israeli Patent Application No. 262097.
Tchounwou P.B., et al., "Heavy metals toxicity and the environment", EXS 2012; 101:133-164.

* cited by examiner

*Primary Examiner* — Terry A McKelvey
*Assistant Examiner* — Catheryne Chen
(74) *Attorney, Agent, or Firm* — Silvia Salvadori, P.C.; Silvia Salvadori

(57) ABSTRACT

Disclosed is the use of cosmetic compositions comprising an oak extract, a grape seed extract and a green tea extract to protect the skin, scalp, hair and external mucosa against air pollutants.

19 Claims, No Drawings

COSMETIC COMPOSITIONS FOR PROTECTION AGAINST AIR POLLUTANTS

This application is a U.S. national stage of PCT/EP2017/058247 filed on 6 Apr. 2017, which claims priority to and the benefit of Italian Application No. 102016000036493 filed on 8 Apr. 2016, the contents of which are incorporated herein by reference in their entireties.

TECHNICAL FIELD OF INVENTION

The present invention relates to cosmetic compositions comprising an oak extract, a grape seed extract and a green tea extract which are useful to protect against air pollutants.

STATE OF THE ART

It has long been known that air pollution has a significant impact on human health, and a number of specific warnings to that effect have recently been issued by the authorities. For example, in 2014 the US Environmental Protection Agency reported that over 142 million Americans live in areas wherein the air quality does not meet the National Ambient Air Quality Standards (https://www.epa.gov/airtrends).

In the same year, the WHO attributed 7 million premature deaths to air pollution exposure (http://who.int/mediacentre/news/releases/2014/air-pollution/en/), and there is increasing evidence that air pollutants have a damaging effect on the internal organs (*Curr. Vasc. Pharmacol.*, 2006, 4, 199-203).

In addition to the internal organs, among which the respiratory tract is obviously the main target for air pollutants (*Annu. Rev. Public Health*, 1994,15,107-132), the skin is one of the most exposed target organs, due to its large surface and continual exposure.

To date, the environmental impact on skin health has mainly been evaluated in terms of the effect on the skin of ultraviolet radiation from sunlight (*J. Invest. Dermatol.*, 2003, 120, 1087-1093; *Prog. Biophys. Mol. Biol.*, 2006, 92, 119-131); however, in addition to UV radiation, pollution also includes organic and inorganic substances which can potentially involve a further risk to skin health.

Among the environmental pollutants, various chemical classes have been identified, ranging from gaseous pollutants such as NO, CO and $SO_2$ and volatile organic compounds (VOC) to persistent organic pollutants (including pesticides and dioxin-like compounds).

Moreover, particulate matter (a complex mixture of drops of liquids and/or solids in suspension in gas, while heavy metals like cadmium, lead, chromium and mercury are common air pollutants) is a source of health risk due to bioaccumulation, as it is typically absorbed by carbon particles suspended in the air, and can penetrate the skin and be accumulated (*Environ. Pollut.* 2008 151, 362-367).

In the absence of explanations of the overall mechanism whereby environmental pollutants can damage the skin, some mechanisms have been identified as the primary cause of skin damage on the basis of the currently available data. Said mechanisms, which mainly relate to heavy metals, include:
- generating free radicals (*J. Toxicol. Cut & Ocular Toxicol.*, 1987, 6(3), 183-191);
- inducing the inflammatory cascade (powders containing heavy metals have been found to increase gene expression of pro-inflammatory cytokines) (*Toxicol. Lett.*, 1999, 105, 92-99);
- reducing the natural defence mechanisms.

The external tissues of the skin are those most exposed to air pollutants, which (especially heavy metals) reduce the cell defences against free radicals. Heavy metals therefore exacerbate the toxic effects of all the other gaseous pollutants, because they reduce the efficacy of the natural defence mechanisms and accelerate skin aging.

It has been demonstrated that these events leads, in particular, to accelerated extrinsic skin aging (with an increase in the formation of wrinkles and dark patches) (*Biol. Chem.*, 2010, 391, 1235-1248; *J. Investig. Dermatol.* 2010, 130, 2719-2726) and an increase in atopic dermatitis (*Allergy*, 1996, 51, 532-539).

Although further extensive research is required to fully understand the mechanisms whereby air pollutants exert harmful effects on the skin, it should be noted that, in view of the limited scientific evidence, there are no guidelines designed to protect the scalp and hair from air pollution, apart from limiting exposure thereto (*JEADV*, 2015, 29, 2326-2332).

In view of the factors set out above, there is still a need to found cosmetic compositions that effectively protect the skin, scalp, hair and external mucosa in particular against air pollutants.

SUMMARY OF THE INVENTION

The present invention relates to cosmetic compositions comprising an oak extract, a grape seed extract and a green tea extract which are useful to protect the skin, scalp, hair and external mucosa against air pollutants.

DESCRIPTION OF THE INVENTION

The present invention relates to the use of cosmetic compositions comprising an oak extract, a grape seed extract and a green tea extract which are useful to protect the skin, scalp, hair and external mucosa against air pollutants.

According to a preferred embodiment, the compositions according to the invention are useful to protect the external mucosa, especially that of the nose and mouth (such as the lips).

The oak extract (Q) is preferably an extract characterised by a total polyphenol content ranging between 30% and 60% w/w, more preferably equal to or greater than 45% w/w. The oak extract (Q) is preferably an aqueous dry extract.

According to a preferred embodiment, the oak extract can be obtained from bark.

The oak extract may be present in the composition in amounts ranging from 0.01% to 5% w/w, preferably from 0.05% to 1% w/w, more preferably amounts to 0.25% w/w, and even more preferably is 0.1% w/w.

The grape seed (GS) extract is preferably an extract characterised by a total proanthocyanidin content (calculated by the Folin method and expressed as catechins) equal to or greater than 95% w/w and a monomer content (resulting from the sum of catechin and epicatechin expressed as catechin) ranging between 5 and 15% w/w evaluated by the HPLC method, and is more preferably an aqueous dry extract.

The grape seed extract may be present in the composition in amounts ranging from 0.01% to 5% w/w, preferably from 0.05% to 1% w/w, more preferably amounts to 0.25% w/w, and even more preferably is 0.1% w/w.

The green tea (GT) extract is preferably an extract characterised by a polyphenol content (calculated by the Folin method and expressed as catechins) equal to or greater than 40% w/w, and a catechin content (expressed as epicatechin-3-O-gallate), evaluated by the HPLC method, equal to or greater than 15% w/w, and is more preferably an aqueous dry extract.

According to a preferred embodiment, the green tea extract can be obtained from the leaves.

The green tea extract may be present in the composition in amounts ranging from 0.01% to 5% w/w, preferably from 0.05% to 1% w/w, more preferably amounts to 0.25% w/w, and even more preferably is 0.1% w/w.

All the extracts are commercially available or can be easily prepared by the skilled person using known techniques.

The compositions may preferably be administered topically.

Formulations comprising the compositions according to the invention can be obtained by conventional techniques as described, for example, in "Remington's Pharmaceutical Handbook", Mack Publishing Co., N.Y., USA.

Examples of topical formulations are emulsions, gels, foundations, lipsticks and ointments.

It has now surprisingly been found that compositions containing an oak extract, a grape seed extract and a green tea extract show a protection activity on the skin, scalp, hair and external mucosa against air pollutants greater than that obtainable when the extracts are used separately, thus demonstrating a synergic activity. This is supported by the results of the experimental studies conducted.

In particular, the compositions according to the invention have proved useful in reducing the harmful effects induced by heavy metals as air pollutants.

The examples below further illustrate the invention.

EXAMPLES

Formulation Example 1

| Ingredients (Tradename) | INCI name | % |
|---|---|---|
| Demineralised water | Aqua (Water) | 65.450 |
| Acemulgor A | Cetyl Alcohol, C12-20 Acid PEG-8 Ester | 14.000 |
| Nexbase 2006 | Hydrogenated polydecene | 6.000 |
| Syntewax MS 2000 | PEG-90 Stearate, Glyceryl stearate | 4.500 |
| Myritol 318 | Caprylic/capric Triglyceride | 4.000 |
| Glycerin | Glycerin | 3.000 |
| Grape seed extract GS | | 0.250 |
| Oak extract Q | | 0.250 |
| Green tea extract GT | | 0.250 |
| ABIL 350 | Dimethicone | 1.000 |
| Phenoxyethanol | Phenoxyethanol | 0.600 |
| Polysorbate 60 | Polysorbate-60 | 0.250 |
| Bioscontrol Element | Imidazolidinyl urea | 0.300 |
| Disodium EDTA | Disodium EDTA | 0.100 |
| Aperoxid TLA | Lecithin, Tocopherol, Ascorbyl palmitate, Citric acid | 0.050 |

The experiments conducted to evaluate the protective efficacy of the cosmetic composition of Example 1 and of the extracts used individually, in amounts equal to that present in the composition, are described below.

Example 2—Evaluation of Efficacy on Cell Viability

The experimental model used in this test is represented by human skin-derived fibroblasts (ATCC-CRL-2703). The cells were cultured in complete DMEM medium with 10% fetal bovine serum and maintained in an incubator at 37° C., 5% $CO_2$. The cells were grown to confluence for carrying out the tests. For carrying out the tests, human fibroblast cultures were treated for 24 hours with a mixture of heavy metals (Pb-Ef-Cr, each metal 90 µM), which are known pollutants typically present under air-dispersed pollution conditions. At the same time as the environmental damage, the cell cultures were treated with the test products at 3 concentrations, selected among those which did not prove cytotoxic on the preliminary cytotoxicity test.

The cell cultures were exposed to the samples for 48 hours. At the end of the test period, cell viability was evaluated by MTT assay. The MTT assay (3-(4,5-dimethyl-thiazol-2-yl)-2,5-diphenyltetrazolium bromide) is a simple, accurate, standard colorimetric method for measurement of cell viability. The assay is based on intracellular reduction of yellow tetrazolium salts by the mitochondrial enzyme succinate dehydrogenase to blue/purple formazan crystals. The reaction can therefore only take place in metabolically active cells, and the optical density value obtained from a spectrophotometric reading can be correlated with the quantity of viable cells present. At the end of each treatment, all wells were washed with PBS, stained with an 0.5 mg/mL MTT solution and incubated for three hours in an atmosphere at 36.5° C./5% $CO_2$. The wells were then treated with isopropanol and incubated for two hours at room temperature. After incubation the absorbance readings were taken at 570 nm in the microplate reader (the isopropanol solution being used as blank). For each experimental condition, the ratio between the mean optical density of the treated cultures and the mean optical density of the negative controls determines the cell viability rate.

The results were compared with the negative control cultures (untreated, CTR−) and the positive control cultures (treated with heavy metals only, CTR+). The treatments were conducted in triplicate.

The table below (Table 1) shows the results expressed as protein content and as % protection compared with the positive control. The statistically significant t-test values are indicated by (*) for $p<0.05$ and (**) for $p<0.95$.

TABLE 1

| | % cell viability | % protection vs CTR(+) |
|---|---|---|
| CTR(−) | 100 | — |
| CTR(+) | 55.9 | — |
| GS 0.001% | 61.18 | 11.97* |
| GS 0.005% | 68.90 | 29.4* |
| Q 0.001% | 57.02 | 2.54 |
| Q 0.005% | 61.62 | 12.97* |
| TV 0.001% | 60.18 | 9.70 |
| TV 0.005% | 65.5 | 21.7* |
| GS 0.001% + Q 0.001% + TV 0.001% | 78.9 | 52.15** |
| GS 0.005% + Q 0.005% + TV 0.005% | 97.5 | 94.33** |

Example 3—Evaluation of Efficacy on Cell Metabolism (Protein Content)

The experimental model used in this test is represented by human skin-derived fibroblasts (ATCC-CRL-2703). The cells were cultured in complete DMEM medium with 10% fetal bovine serum and maintained in an incubator at 37° C., 5% $CO_2$. The cells were grown to confluence for carrying out the tests. For carrying out the tests, human fibroblast cultures were treated for 24 hours with a mixture of heavy metals (Pb-Ef-Cr, each metal 90 μM), which are known pollutants typically present under air-dispersed pollution conditions. At the same time as the environmental damage, the cell cultures were treated with the test products at 3 concentrations, selected among those which did not prove cytotoxic on the preliminary cytotoxicity test.

The cell cultures were exposed to the samples for 48 hours. At the end of the test period the cell metabolism was evaluated by assaying the protein content in the culture media.

Said evaluation was conducted by the Lowry colorimetric method on the cell culture media. The Lowry assay uses the same principle as the biuret method, i.e. the reaction whereby in an alkaline medium, Cu+ ions complex to the proteins and catalyze the oxidation process of tyrosine and tryptophan residues. Said oxidation generates reduction of the Folin-Ciocalteu reagent which, from the characteristic yellow colour, turns blue; the darker the blue colour, the more proteins are present in the biological matrix. The quantitative determination uses a calibration curve constructed with increasing known concentrations of standard albumin.

The table below shows the results expressed as protein content and as % protection compared with the positive control. The statistically significant t-test values are indicated by (*) for p<0.05 and (**) for p<0.95.

TABLE 2

| | Protein content (μg) | % protection vs CTR(+) |
|---|---|---|
| CTR(−) | 52.12 ± 2.21 | — |
| CTR(+) | 24.21 ± 1.98 | — |
| GS 0.001% | 27.30 ± 1.52 | 11.07 |
| GS 0.005% | 31.31 ± 1.78 | 25.43* |
| Q 0.001% | 25.93 ± 2.01 | 6.16 |
| Q 0.005% | 27.90 ± 1.85 | 13.22* |
| TV 0.001% | 26.93 ± 1.53 | 9.74 |
| TV 0.005% | 27.83 ± 1.63 | 12.97* |
| GS 0.001% + Q 0.001% + TV 0.001% | 39.12 ± 2.21 | 53.42** |
| GS 0.005% + Q 0.005% + TV 0.005% | 50.90 ± 2.05 | 95.62** |

As clearly demonstrated by the examples above, the effect obtainable by administering the compositions according to the invention is greater than the sum of the individual effects obtainable by administering the oak, grape seed and optionally green tea extracts separately. In other words, the interaction between the individual active ingredients produces an evident synergic effect.

The invention claimed is:

1. A non-therapeutic method of protecting skin, scalp, hair and external mucosae from air pollutants of individuals in need thereof with compositions comprising, as active ingredients, an oak extract, a grape seed extract and a green tea extract, wherein the air pollutants are heavy metals, said method comprising topically administering said compositions to said individuals.

2. The method according to claim 1, wherein the external mucosae are nasal or oral mucosae.

3. The method according to claim 2, wherein the external mucosae are lips.

4. The method according to claim 1, wherein the oak extract is characterised by a total polyphenol content ranging from 30% to 60% w/w.

5. The method according to claim 1, wherein the oak extract is characterised by a total polyphenol content equal to or greater than 45% w/w.

6. The method according to claim 1, wherein the oak extract is present in amounts ranging from 0.01% to 5% w/w.

7. The method according to claim 1, wherein the oak extract is present in amounts ranging from 0.05% to 1% w/w.

8. The method according to claim 1, wherein the oak extract is present in amounts equal to 0.25% w/w.

9. The method according to claim 1, wherein the oak extract is present in amounts equal to 0.1% w/w.

10. The method according to claim 1, wherein the grape seed extract is characterised by a total proanthocyanidin content calculated by the Folin method and expressed as catechins equal to or greater than 95% w/w, and a monomer content resulting from the sum of catechin and epicatechin expressed as catechin ranging from 5% to 15% w/w.

11. The method according to claim 1, wherein the grape seed extract is present in amounts ranging from 0.01% to 5% w/w.

12. The method according to claim 1, wherein the grape seed extract is present in amounts ranging from 0.05% to 1% w/w.

13. The method according to claim 1, wherein the grape seed extract is present in amounts equal to 0.25% w/w.

14. The method according to claim 1, wherein the grape seed extract is present in amounts equal to 0.1% w/w.

15. The method according to claim 1, wherein the green tea extract is characterised by a polyphenol content calculated by the Folin method and expressed as catechins equal to or greater than 40% w/w and a catechin content expressed as epicatechin-3-O-gallate equal to or greater than 15% w/w.

16. The method according to claim 1, wherein the green tea extract is present in amounts ranging from 0.01% to 5% w/w.

17. The method according to claim 1, wherein the green tea extract is present in amounts ranging from 0.05% to 1% w/w.

18. The method according to claim 1, wherein the green tea extract is present in amounts equal to 0.5% w/w.

19. The method according to claim 1, wherein the green tea extract is present in amounts equal to 0.1% w/w.

* * * * *